United States Patent [19]
Morales et al.

[11] Patent Number: 5,591,724
[45] Date of Patent: Jan. 7, 1997

[54] METHOD FOR TREATING THE URINARY BLADDER AND ASSOCIATED STRUCTURES USING HYALURONIC ACID

[75] Inventors: Alvaro Morales, Kingston; Stanley J. Alkemade, Seaforth, both of Canada

[73] Assignee: Bioniche Inc., Canada

[21] Appl. No.: 388,038

[22] Filed: Feb. 14, 1995

[51] Int. Cl.$^6$ .......................... A61K 31/73; A61K 47/36
[52] U.S. Cl. .......................... 514/54; 514/777; 514/891; 536/55.1; 536/123.1
[58] Field of Search ........................ 514/54, 777

[56] References Cited

U.S. PATENT DOCUMENTS

| | | |
|---|---|---|
| 4,296,104 | 10/1981 | Herschler . |
| 4,302,577 | 11/1981 | Rucker . |
| 4,524,066 | 6/1985 | Wolf . |
| 4,640,912 | 2/1987 | Hausman . |
| 4,711,780 | 12/1987 | Fahim . |
| 4,820,693 | 4/1989 | Gillespie . |
| 4,879,282 | 11/1989 | Saliba, Jr. . |
| 4,966,890 | 10/1990 | Gillespie . |
| 5,037,810 | 8/1991 | Saliba, Jr. . |
| 5,180,715 | 1/1993 | Parsons . |
| 5,290,271 | 3/1994 | Jernberg ......................... 604/891.1 |
| 5,356,883 | 10/1994 | Kuo et al. ....................... 514/54 |

FOREIGN PATENT DOCUMENTS

| | | |
|---|---|---|
| 557118 | 8/1993 | European Pat. Off. . |
| 572932 | 12/1993 | European Pat. Off. . |
| 9117777 | 11/1991 | WIPO . |
| 9421299 | 9/1994 | WIPO . |
| 9425080 | 11/1994 | WIPO . |

OTHER PUBLICATIONS

Kiesewetter et al 2Eit. Urol. Nephrol. 58(10):735–738 (1965).
Gill et al J. Urol. 127(1):152–154 (1982).
Wakasuki et al J. Urol. 133(2): 319–323 (1985).
Holm–Bentzen et al Neurol. Urodyn. 5(6):519–523 (1986).
Hurst et al J. Urol. 138(2):433–437 (1987).
Maroudas et al Brit. J. Urol. 59(6):519–522 (1987).
Laurent et al Cell Tissue Res. 279(2):241–248 (1985).
Stewart et al., "The Use of Dimethyl Sulfoxide (DMSO) in the Treatment of Interstitial Cystitis," *J. Urology*, Vol. 98, pp. 671–672 (1968).
Strohmaier et al Helv. Chir. Acta 56(3):323–325 (1989).
Parsons et al., "Decreased Urinary Uronic Acid Levels in Individuals with Interstitial Cystitis," *J. Urology*, Vol. 143, pp. 690–693 (1990).
Fleischmann et al., "Clinical and Immunological Resonse to Nifedipine for the Treatment of Interstitial Cystitis," *J. Urology*, vol. 146, pp. 1235–1239 (1991).
Nickel et al., "The Bladder Mucus (Glycosaminoglycan) Layer in Interstitial Cystitis," *J. Urology*, vol. 149, pp. 716–718 (1993).
Hanno et al., "Conservative Therapy of Interstitial Cystitial," *Seminars in Urology*, vol. 9, No. 2, pp. 143–147 (1991).
Chelsky et al., "Bladder Permeability in Interstitial Cystitis is Similar to that of Normal Volunteers: Direct Measurement by Transvesical Absorption of 99m Technetiumdiethylenetriaminepentaacetic Acid," *J. Urology*, vol. 151, pp. 346–349 (1994).
Eldrup et al., "Permeability and Ultrastructure of Human Bladder Epithelium," *Br. J. Urology*, vol. 55, pp. 488–492 (1983).
Brandt, "The Effect of Synovial Hyaluronate on the Injestion of Monosodium Urate Crystals by Leukocytes," *Clinica Chimica Acta*, vol. 55, pp. 307–315 (1974).
Messing et al., "Interstitial Cystitis," *Urology*, vol. 12, No. 4, pp. 381–392 (1978).
Balazs et al., "The Effect of Hyaluronic Acid on Fibroblasts, Mononuclear Phagocytes and Lymphocytes," *Biology of Fibroblasts*, Academic Press, pp. 237–252 (1973).
Kuwahara et al., "Bacterial Infection and Acid Mucopolysaccharides in Epithelium of Rat Urinary Bladder," *Urological Research*, vol. 10, No. 2, pp. 93–96 (1982).

*Primary Examiner*—Shep K. Rose
*Attorney, Agent, or Firm*—Jones & Askew

[57] ABSTRACT

A method of treating interstitial cystitis comprising contacting the internal bladder and associated structures in a mammal having interstitial cystitis with a solution containing hyaluronic acid having a molecular weight of not less than approximately $2 \times 10^5$ Daltons in a concentration effective to treat the interstitial cystitis.

6 Claims, No Drawings

METHOD FOR TREATING THE URINARY BLADDER AND ASSOCIATED STRUCTURES USING HYALURONIC ACID

TECHNICAL FIELD

The present invention relates to a novel method for treating the internal bladder and associated structures in a mammal comprising the step of contacting the internal bladder and associated structures in the mammal with a solution containing hyaluronic acid having a molecular weight of not less than approximately $2 \times 10^5$ Daltons. More particularly, the present invention relates to a novel method for treating the internal bladder and associated structures in a mammal having interstitial cystitis comprising the step of contacting the internal bladder and associated structures in the mammal having interstitial cystitis with a solution containing hyaluronic acid having a molecular weight of not less than approximately $2 \times 10^5$ Daltons in a concentration effective to treat the interstitial cystitis.

BACKGROUND OF THE INVENTION

In mammals, the unique tight junctions of bladder surface epithelial cells are the fundamental mechanism by which the bladder maintains its impermeability. However, the glycosaminoglycan layer on the luminal surface of the bladder wall may be an important defense mechanism for protecting the transitional epithelium from urinary irritants (Chelsky, M. et al. 1994. Journal of Urology, 151:346.). This glycosaminoglycan layer consists of mucopolysaccharides attached to a core protein that, in turn, is bound to a central hyaluronic acid string. This highly viscous, highly hydrophilic glycosaminoglycan layer protects the transitional epithelium of the bladder from irritants in the urine including, but not limited to, pathogens, microcrystals, proteins, calcium and carcinogens (Nickel, J. C. et al. 1993. Journal of Urology, 149:716). This glycosaminoglycan layer also prevents small, uncharged molecules such as urea from diffusing to and across the transitional epithelium. Thus, the glycosaminoglycan layer lining the bladder acts as a barrier between the environment within the lumen of the bladder, and the transitional epithelium of the bladder and protects this transitional epithelium from inflammation, infection, trauma, stone formation and carcinogenesis.

Interstitial cystitis is a poorly understood bladder condition for which there is no universal effective treatment program (Fleischmann, J. D. et al. 1991. Journal of Urology, 146:1235). Symptoms include urgency for urination, increased frequency of urination and suprapubic pain usually relieved by voiding. Other symptoms include arthritis, spastic colon and low grade fever. Individuals with interstitial cystitis can be significantly disabled, and individuals with advanced interstitial cystitis can require major surgery in order to function. Although the etiology of interstitial cystitis remains unexplained, it has been suggested that abnormalities of or deficiencies in the glycosaminoglycan layer lining the transitional epithelium of the bladder may be a primary defect. (Eldrup J. 1983. British Journal of Urology. 55:488). These abnormalities or deficiencies may enable increased permeability of the transitional epithelium (Parsons, E. L. et al. 1990. Journal of Urology, 143:690) and this increased permeability may enable urinary solutes to gain access to the subepithelial tissue and to induce an irritative, inflammatory response that contributes to the symptoms of interstitial cystitis. Therefore, as interstitial cystitis may be related to an abnormality or deficiency in the glycosaminoglycan layer lining the transitional epithelium of the bladder, temporary replacement of this defective glycosaminoglycan layer with a defined glycosaminoglycan that protects the transitional epithelium may be effective in the treatment of interstitial cystitis.

There is no standard treatment for interstitial cystitis. Among the treatments used are hydraulic distention of the bladder, oral amitriptyline or sodium pentosanpolysulfate, intravesical instillation of dimethylsulfoxide, oxychlorosene sodium, silver nitrate, heparin, or of a composition comprising an angiostatic steroid and pentosanpolysulfate. However, both the efficacy and the effectiveness of these treatments is variable.

Hydraulic distention of the bladder is done under general or spinal anesthesia for one to two minutes at a pressure of 80 to 100 cm $H_2O$. In one study using hydraulic distention of the bladder to treat interstitial cystitis, less than 55% of the patients treated reported relief immediately after treatment and only 2% reported relief six months after treatment (Hanno P. M. et al. 1991. Semin Urology, 9:143).

Instillation of dimethylsulfoxide (DMSO) into the bladder for six to eight weeks resulted in a 53% response rate to DMSO versus an 18% response rate to placebo, with the average length of response being six months (Perez-Marrero, R. et al. 1967. Journal of Urology, 98: 671). Pharmacological effects of DMSO include membrane penetration, enhanced drug absorption, anti-inflammatory and analgesic effects, collagen dissolution, muscle relaxation and mast cell histamine release. Side effects include increased vesicle irritability and garlic-like breath odor.

Equivalent results to instillation of DMSO have been reported with oxychlorosene sodium (Messing, E. M. et al. 1978. Urology, 12:381). However instillation of oxychlorosene sodium requires anesthesia because of intense discomfort.

Sodium pentosanpolysulfate is a low molecular weight synthetic glycosaminoglycan (U.S. Pat. No. 4,524,066 to Wolf) and is characterized by very low viscosity and high electronegativity.

U.S. Pat. No. 4,820,693 to Gillespie (Gillespie '693) discloses a composition and method for arresting angiogenesis and cell, capillary or membrane leakage comprising either oral or intravesical administration of an angiostatic steroid and pentosanpolysulfate. The molecular weight of the pentosanpolysulfate for use in Gillespie '693 is between $1.6 \times 10^3$ and $6 \times 10^3$ Daltons, and is preferably about $2 \times 10^3$ Daltons. U.S. Pat. No. 4,966,890 to Gillespie (Gillespie '890) discloses a composition and method for treating interstitial cystitis comprising either oral or intravesical administration of an angiostatic steroid and pentosanpolysulfate. Gillespie '890 teaches that pentosanpolysulfate can be used in place of heparin and that pentosanpolysulfate, in combination with an angiostatic steroid, cures interstitial cystitis by arresting angiogenesis, cell membrane leakage and capillary leakage or exchange in the bladder.

U.S. Pat. No. 5,180,715 to Parsons (Parsons '715) also discloses the use of pentosanpolysulfate for treating interstitial cystitis. Parsons '715 provides data to show that oral pentosanpolysulfate at doses in excess of 100 mg per day are most effective for treating interstitial cystitis. Parsons '715 also suggests, but provides no data to show, that intravesical instillation of pentosanpolysulfate is useful for treating interstitial cystitis. Parsons '715 teaches that pentosanpolysulfate can be used in place of heparin and that pentosanpolysulfate acts to block bacterial adherence to the transitional epithelium of the bladder.

Pentosanpolysulfate as disclosed in Gillespie '693, in Gillespie '890 and in Parsons '715 is a low viscosity glycosaminoglycan. As interstitial cystitis may be related to a defect in the high viscosity glycosaminoglycan layer on the luminal surface of the bladder, intravesical administration of the low viscosity pentosanpolysulfate would not provide adequate protection to the transitional epithelium of the bladder and associated structures. Therefore, what is needed is a highly viscous, highly hydrophilic substance which will coat the transitional epithelium of the bladder and associated structures. Such a highly viscous, highly hydrophilic substance can provide a barrier between irritants within the lumen of the bladder and associated structures and the transitional epithelium lining the bladder and associated structures.

Hyaluronic acid (HA) is a heteropolysaccharide consisting of alternating residues of D-glucuronic acid and N-acetylglucosamine. HA is a linear polymer with a molecular weight of up to $13 \times 10^6$ Daltons. It is found in connective tissue, in joint synovial fluid, in ocular vitreous humor, in umbilical cord, in cocks comb and is synthesized by some bacteria including, but not limited to streptococcal species. High molecular weight HA inhibits lymphocyte migration (Balzas E. A. et al. 1973. In: Biology of Fibroblasts. Academic Press. pp. 237–252), and the phagocytic and chemotactic capacities of neutrophils and leukocytes are also inhibited. (Brandt, K. D. 1974. Clinical Chemical Acta 55:307).

HA is highly viscous, highly electronegative and highly hydrophilic. It has been found that a high molecular weight fraction of HA provides unexpectedly excellent results in the treatment of interstitial cystitis.

SUMMARY OF THE INVENTION

Briefly, the present invention comprises a method for treating interstitial cystitis in a mammal with interstitial cystitis comprising the step of contacting the internal surface of the bladder and associated structures which include the ureters and urethra in a mammal having interstitial cystitis with a solution containing HA having a molecular weight of not less than approximately $2 \times 10^5$ Daltons in a concentration effective to treat the interstitial cystitis.

This invention also includes a method for treating bladder trauma, bladder irritation and bladder infection in a mammal with bladder trauma, bladder irritation or bladder infection comprising the step of contacting the internal surface of the bladder and associated structures in a mammal having bladder trauma, bladder irritation or bladder infection with a solution containing HA having a molecular weight of not less than approximately $2 \times 10^5$ Daltons in a concentration effective to treat the bladder trauma, bladder irritation or bladder infection.

This invention further comprehends the addition of various substances including, but not limited to, antibiotics, bacterial cell extracts, viruses, cytokines and interferons to the HA composition for use in treating interstitial cystitis, bladder trauma, bladder irritation and bladder infection.

It is an object of the present invention to provide a method for treating interstitial cystitis in a mammal with interstitial cystitis by contacting the internal surface of the bladder and associated structures with a solution containing HA having a molecular weight of not less than approximately $2 \times 10^5$ Daltons in a concentration effective to treat the interstitial cystitis.

It is also an object of the present invention to provide a method for treating trauma, irritation and infection of the lining of the renal pelvis, ureters, bladder and urethra in a mammal with trauma, irritation and infection of the lining of the renal pelvis, ureters, bladder and urethra by contacting the internal surface of the renal pelvis, ureters, bladder and urethra with a solution containing HA having a molecular weight of not less than approximately $2 \times 10^5$ Daltons in a concentration effective to treat the trauma, irritation and infection of the lining of the renal pelvis, ureters, bladder and urethra.

Other objects, features and advantages of the present invention will become apparent upon reading the following detailed description of the preferred embodiment of the invention when taken in conjunction with the appended claims.

DETAILED DESCRIPTION OF THE INVENTION

As used herein, the phrase "internal surface of the bladder" refers to the surface of the bladder which is lined by transitional epithelium.

As used herein, the phrase "associated structures" refers to the ureters and urethra.

The present invention is directed to a method for treating interstitial cystitis in a mammal with interstitial cystitis by contacting the internal surface of the bladder and associated structures with a solution containing HA having a molecular weight of not less than approximately $2 \times 10^5$ Daltons in a concentration effective to treat the interstitial cystitis. It has been discovered that HA and salts thereof, having a molecular weight of not less than approximately $2 \times 10^5$ Daltons, unexpectedly, is successful in treating interstitial cystitis in a mammal with interstitial cystitis.

The HA for use in this invention has a molecular weight of not less than approximately $2 \times 10^5$ Daltons. More preferably the HA has a molecular weight between approximately $6 \times 10^5$ and $7.3 \times 10^5$ Daltons. Most preferably the HA has a molecular weight of between approximately $6.0 \times 10^5$ and $7.0 \times 10^5$ Daltons.

Various methods for obtaining molecular weight fractions of HA are available. These include fractionation of HA prepared from cartilage, fractionation of HA produced from bacterial fermentation and purchase of molecular weight fractions of HA from commercial sources including, but not limited to Fluka Chemical Corporation, 908 South Second Street, Ronkonkoma, N.Y. 11779 and Genzyme Corporation, One Kendall Square, Cambridge, Mass. 02139.

The HA for use in the present invention is present in a concentration from about 0.01 mg/ml to about 25 mg/ml. More preferably the HA is present in a concentration from about 0.1 mg/ml to about 2 mg/ml. Most preferably the HA is present in a concentration from approximately 0.4 mg/ml to about 1.2 mg/ml. The HA is solubilized in a pharmaceutically acceptable buffer including, but not limited to, physiological saline and phosphate buffered saline. However, it is to be understood that any of the physiological buffers known to those skilled in the art to be pharmaceutically acceptable for contacting the surface of the bladder and associated structures in a mammal can be used in the present invention.

The HA solution for use in the present invention may further include an antibiotic effective for treating interstitial cystitis. Determination of the antibiotic and of the amount of the antibiotic to be included in the HA solution are well within the determination of those skilled in the art. The HA solution for use in the present invention may further include an immunotherapeutic agent including, but not limited to bacterial cell extracts such as mycobacterial cell wall extract and bacilli calmette-guerin, viruses, cytokines and interferons.

The HA solution for use in the present invention is instilled into the bladder and associated structures in a volume of between approximately 5 ml and 100 ml. More preferably the HA composition is instilled into the bladder and associated structures in a volume of between approximately 20 ml and 70 ml. Most preferably, the HA composition is instilled into the bladder and associated structures in a volume of between approximately 40 and 60 ml.

The amount of HA to be instilled into the bladder and associated structures in the present invention is between approximately 5 mg and 100 mg. More preferably the amount of HA to be instilled into the bladder and associated structures is between approximately 20 mg and 60 mg. Most preferably the amount of HA to be instilled into the bladder and associated structures is between approximately 35 mg and 45 mg.

The HA solution of the present invention may be administered from a container such as, but not limited to, a bottle. The HA composition may instilled into the bladder and associated structures using a urinary catheter. However, it is to be understood that any method known to those skilled in the art for contacting the internal surface of the bladder and associated structures in a mammal with a pharmaceutical solution can be used in the present invention.

The HA solution should remain in contact with the bladder and associated structures for from approximately 30 minutes to 8 hours. More preferably from 30 minutes to 4 hours. Most preferably from 30 minutes to 2 hours.

Treating interstitial cystitis in a mammal having interstitial cystitis with a solution containing HA by contacting the internal bladder and associated structures with HA and salts thereof, having an average molecular weight of not less than approximately $2 \times 10^5$ Daltons, provides surprisingly good results in providing relief from the symptoms of interstitial cystitis without disturbing side effects.

EXAMPLE 1

ISOLATION, PURIFICATION AND FRACTIONATION OF HYALURONIC ACID

The following describes a method for the isolation, purification and fractionation of hyaluronic acid from cartilage for use in this invention.
Pre-Treatment of Cocks Combs
The preparation of sodium hyaluronate from frozen or fresh cocks combs involves the following steps: The cocks combs are minced, homogenized, dehydrated in acetone, and vacuum dried to a dry powder. The water content of the discarded acetone is less than 2.0%. The powder is digested enzymatically with papain in a buffered aqueous medium containing cysteine hydrochloride. The resulting mixture is clarified and ultrafiltered using a membrane with a molecular weight exclusion limit of $3 \times 10^4$ Daltons. The retained clear liquid has a pH between 5.0 and 7.0. The mucopolysaccharide content is 2.0 and 6.0 mg/ml sodium hyaluronate as determined by glucuronic acid assay. The amino acid content is greater than 6.0 mg/ml as determined by ninhydrin assay.
Complexing, Fractionation, Precipitation
NaCl (up to 0.1 M) and cetyl-pyridinium chloride (CPC) are added to the clear liquid with agitation. The precipitate is collected by centrifugation and washed three times in 0.01 M NaCl with 0.05% CPC. The precipitate is suspended in 0.05 M NaCl with 0.05% CPC with agitation and the cloudy supernatant is eliminated. This procedure is repeated several times using 0.1 M NaCl with 0.05% CPC. The precipitate is then dispersed in 0.3 M NaCl with 0.05% CPC with agitation and the extraction is repeated three times. The precipitate is then eliminated. The clear supernatants are pooled, brought to 0.23 M NaCl, CPC is added, the mixture is treated with Celite(R), and filtered. After Celite(R) treatment, the sodium hyaluronate content is 2.5–5.0 mg/ml as determined by glucuronic acid assay.
Isolation of Hyaluronic Acid
The filtrate is ultrafiltered using a membrane with a molecular weight exclusion limit of $3 \times 10^4$ Daltons and the retained liquid is concentrated. This liquid is precipitated with 95% ethanol and centrifuged. The precipitate is dissolved in 0.1 M NaCl and precipitated again with 95% ethanol. The precipitate is collected and washed yielding a crude product having an average molecular weight of not less than approximately $2.5 \times 10^5$ Daltons. The yield is equivalent to 0.6% of original fresh tissue.
Purification of Hyaluronic Acid Fraction
The precipitate is dissolved in pyrogen-free distilled water (10 mg/ml) and ultrafiltered using a membrane with a molecular weight exclusion limit of $2 \times 10^5$ Daltons without addition of supplementary water. This increases the concentration of molecules having a molecular weight greater than $2 \times 10^5$ Daltons. Ultrafiltration is used to reduce the volume to 10% of original volume. Water is added to the concentrated solution and the operation is repeated twice. The concentrated solution is collected and is diluted with water to a concentration of 5 mg/ml hyaluronic acid. NaCl is added to bring the solution to 0.1 M and the solution is precipitated with four volumes of 95% ethanol. The precipitate is washed and then vacuum dried.

This purified hyaluronic acid is polydisperse and has an average molecular weight, of not less than approximately $2\times10^5$ Daltons. Methods for further fractionating this HA into different molecular weight fractions are well known to those of ordinary skill in this art. Further methods for preparing purified HA of the molecular weights claimed in this invention are disclosed in U.S. Pat. No. 4,141,973 to Balzas which is incorporated by reference.

EXAMPLE 2

INTERSTITIAL CYSTITIS PILOT STUDY

In this pilot study five patients with interstitial cystitis, receive intravesical instillation of 40 mg of hyaluronic acid having a molecular weight of $6.5\times10^5$ Daltons in 40 ml to 70 ml sterile saline (USP).

Outcome criteria for this pilot study are related to improvement of symptoms based on decreases in pre-therapy symptoms, pre-therapy pain, and pre-therapy urgency.

SUBJECT 1

PATIENT JM

Interstitial cystitis patient JM (#002) fails treatment with both intravesical heparin instillation and oral pentosanpolysulfate. JM is treated according to the study protocol. Forty mg of HA having a molecular weight of approximately $6.5\times10^5$ Daltons in 50 ml of normal saline (USP) is instilled into the bladder under sterile conditions using a urethral catheter. The catheter is removed and the HA solution is maintained in the bladder for 30 minutes. The treatment is repeated weekly for 7 weeks After the 7th treatment, the patient reports a marked improvement in suprapubic pain and in urgency of urination. The treatment is repeated 4 times during the following 17 weeks. After the last treatment, the patient reports a 100% improvement in suprapubic pain and improvement in urgency. No side effects of the HA treatment are reported by the patient.

SUBJECT 2

PATIENT GH

Interstitial cystitis patients GH (#003) fails treatment with oral propantheline bromide (2-hydroxyethyl)-diisopropylm-ethylammonium bromide xanthene-9-carboxylate, phenyl-propanolamine hydrochloridene and guaifenesin. GH is treated according to the study protocol. Forty mg of HA having a molecular weight of approximately $6.5\times10^5$ Daltons in 50 ml of normal saline (USP) is instilled into the bladder under sterile conditions using a urethral catheter. The catheter is removed and the HA solution is maintained in the bladder for 60 minutes. The treatment is repeated 4 times during an approximately 12 week period. After the last treatment, the patient reports a 100% improvement in pre-therapy symptoms, pre-therapy pain and pre-therapy urgency. No side effects of the HA treatment are reported by the patient.

SUBJECT 3

PATIENT LB

Interstitial cystitis patient LB (#001) fails treatment with intravesical infusion of DMSO and heparin. LB is treated according to the study protocol. Forty mg of HA having a molecular weight of approximately $6.5\times10^5$ Daltons in 50 ml of normal saline (USP) is instilled into the bladder under sterile conditions using a urethral catheter. The catheter is removed and the HA solution is maintained in the bladder for 45 minutes. The treatment is repeated weekly for 5 weeks with significant improvement in pre-therapy symptoms, pre-therapy pain and pre-therapy urgency. Due to an unrelated illness, treatment is interrupted for approximately 7 weeks and symptoms return. After two subsequent treatments, the patient is again improved. Again, due to an unrelated illness, treatment is interrupted for 13 weeks and symptoms return. After two subsequent treatments, the patient reports no improvement in symptoms and treatment is discontinued at the patients request.

SUBJECT 4

PATIENT MM

Interstitial cystitis patients MM (#004) is treated according to the study protocol. Forty mg of HA having a molecular weight of approximately $6.5\times10^5$ Daltons in 50 ml of normal saline (USP) is instilled into the bladder under sterile conditions using a urethral catheter. The catheter is removed and the HA solution is maintained in the bladder for 50 minutes. The treatment is repeated 9 times over a 22 week period. After the last treatment, the patient reports improvement in pre-therapy symptoms, in pre-therapy pain and in pre-therapy urgency. Although the patient reports no side effects from the HA treatment, the patient elects to discontinue HA treatment.

SUBJECT 5

PATIENT MS

Interstitial cystitis patients MS (#006) is treated according to the study protocol. Forty mg of HA having a molecular weight of approximately $6.5\times10^5$ Daltons in 50 ml of normal saline (USP) is instilled into the bladder under sterile conditions using a urethral catheter. The catheter is removed and the HA solution is maintained in the bladder for 60 minutes. The treatment is repeated weekly for 7 weeks. At the end of the 7th week there is a marked improvement in pre-therapy symptoms, in pre-therapy pain and in pre-therapy urgency. Four maintenance treatments are given during the following 16 months. Throughout and at the end of each of the maintenance treatments, the marked improvement is maintained.

EXAMPLE 3

INTERSTITIAL CYSTITIS STUDY

This study is a randomized, double-blind, placebo-controlled multi-center trial of patients in a two-armed protocol. In this study, 75 patients will be randomized to receive intravesical instillations of hyaluronic acid having a molecular weight of approximately $6.5 \times 10^5$ Daltons (experimental) or intravesical instillations of normal saline (control). Inclusion criteria for this study include:

1. >18 years of age
2. diagnosed with interstitial cystitis
3. untreated or failure of previous treatment
4. two or more of following findings present
   a. suprapublic, urethral, or perineal pain
   b. chronic inflammation or mast cell infiltration on cystoscopy or biopsy with no evidence of malignancy
   c. hydrodistension under anesthesia to 80 to 100 cm $H_2O$ pressure with glomerulations (multiple petechiae), bloody effluent and diminished bladder capacity
   d. sterile bacterial urine cultures and no evidence of acid fast bacilli
   e. decreased compliance on cystometrogram
   f. pain on bladder filling (diminished by emptying)

Exclusion criteria for this study include:

1. benign or malignant bladder tumors
2. evidence of vesicoureteral reflux or urethral diverticulum
3. uterine, cervical, vaginal or urethral cancer, or prior pelvic or bladder radiation
4. UTI, vaginitis, prostatitis
5. bladder or lower ureteral calculi
6. active herpes (herpes virus type II)
7. positive urine cytology
8. cystometrogram capacity >400 cc, absence of sensory urgency or unstable bladder
9. waking frequency <5 in 12 hours
10. neurogenic bladder dysfunction
11. active for interstitial cystitis treatment within 1 month of enrollment in study Outcome criteria for this study include:

1. Complete Response (CR): Improvement of symptoms with a >75% decrease in pre-therapy symptom evaluation, pre-therapy visual analog (VAS) pain scale and pre-therapy visual analog (VAS) urgency scale.
2. Partial Response (PR): Incomplete resolution of symptoms and a 50–74.99% decrease in pre-therapy symptom evaluation, pretherapy VAS pain scale and pre-therapy VAS urgency scale.
3. Failure (F): Incomplete resolution of symptoms with a <50% decrease in pre-therapy symptom evaluation, pre-therapy VAS pain scale and pre-therapy VAS urgency scale.

Treatment protocols for this study include:

Each patient randomized to receive the HA treatment of the present invention receives intravesical instillation of 40 mg of HA having a molecular weight of approximately $6.5 \times 10^5$ Daltons in 50 ml of normal saline (USP). Under sterile conditions, a uretheral catheter is introduced into the bladder and any residual urine is removed and sent for bacterial culture. Fifty ml of the HA composition is instilled into the bladder and the catheter is removed. The patient is asked to retain the HA solution as long as possible, but for a minimum of 30 minutes.

The HA instillation is given 1×/week for 4 weeks followed by maintenance instillation 1×/4 weeks for 20 weeks. Therapy is discontinued at 24 weeks after the first HA instillation. The effects of HA treatment are assessed at weeks 4, 8, 12, 16, 20, 24 and 28 of treatment using a symptom evaluation form, a VAS pain scale score and a VAS urgency scale score.

The long term effects of HA treatment are assessed at weeks 32, 38 and 48 using a symptom evaluation form, a VAS pain scale score, a VAS urgency scale score and a quality of life questionnaire.

Each patient randomized to receive the placebo (normal saline) receives intravesicular instillation of 50 ml of saline 1×/week for 4 weeks and 1×/4 weeks for 8 weeks.

Thus far, results are available for 14 patients entered into the study at variable time points within the study protocol. These results are summarized in TABLE I.

| | | INTERSTITIAL CYSTITIS | | | | | | | | | |
|---|---|---|---|---|---|---|---|---|---|---|---|
| Patient # | Date of 1st Tx (m/d/y) | Week 4 | Week 8 | Week 12 | Week 16 | Week 20 | Week 24 | Week 28 | Week 32 | Week 38 | Week 48 |
| 01 | 940615 | CR | PR | PR | CR | CR | CR | CR | | | |
| 02 | 940728 | PR | CR | PR | CR | PR | | | | | |
| 03 | 940802 | | F | PR | PR | | | | | | |
| 04 | 940916 | F | PR | F | PR | | | | | | |
| 05 | | | | | | | | | | | |
| 06 | 941004 | | F | PR | | | | | | | |
| 07 | 941005 | F | PR | PR | | | | | | | |
| 08 | 941007 | F | PR | | | | | | | | |
| 09 | 941027 | | PR | | | | | | | | |
| 10 | 941026 | PR | PR | CR | | | | | | | |
| 11 | 941106 | F | F | | | | | | | | |
| 12 | 941107 | PR | PR | CR | | | | | | | |
| 13 | 941108 | CR | CR | CR | | | | | | | |
| 14 | 941118 | F | CR | | | | | | | | |
| 15 | 941222 | F | F | | | | | | | | |

Response to Treatment: CR — Complete Response, PR — Partial Response, F — Failure
CR = 75–100%
PR = 50–75%
F = <50%

These findings show that high molecular weight hyaluronic acid instilled into the bladder and associated structures is an effective treatment for interstitial cystitis and ameliorates the symptoms of interstitial cystitis.

Although the invention has been described to reference to particular means, materials and examples, it is to be understood that the invention is not limited to the particulars disclosed and extends to all equivalents within the scope of the claims.

We claim:

1. A method of treating interstitial cystitis comprising the step of contacting the lining of the renal pelvis, ureters, urinary bladder and urethra in a mammal having interstitial cystitis by instillation of a solution containing hyaluronic acid having an average molecular weight of not less than $2 \times 10^5$ Daltons in a concentration from about 0.01 mg/ml to about 25 mg/ml in a volume from about 5 ml to about 100 ml.

2. The method of claim 1, wherein the hyaluronic acid has a molecular weight of between approximately $5.0 \times 10^5$ and $7.3 \times 10^5$ Daltons.

3. The method of claim 2, wherein the hyaluronic acid has a molecular weight of approximately $6.5 \times 10^5$ Daltons.

4. The method of claim 1, wherein the concentration of hyaluronic acid is from approximately 0.1 mg/ml to approximately 2 mg/ml.

5. The method of claim 4, wherein the concentration of hyaluronic acid is from approximately 0.4 mg/ml to approximately 1.2 mg/ml.

6. A method of treating interstitial cystitis comprising the step of contacting the lining of the renal pelvis, ureters, urinary bladder and urethra in a mammal having interstitial cystitis by instillation of a solution containing hyaluronic acid having an average molecular weight of between $5 \times 10^5$ and $7.3 \times 10^5$ Daltons and in a concentration from about 0.4 mg/ml to about 1.2 mg/ml in a volume from about 5 ml to about 100 ml.

* * * * *